(12) United States Patent
Anderson et al.

(10) Patent No.: US 7,201,732 B2
(45) Date of Patent: Apr. 10, 2007

(54) DISPENSING METHOD AND DEVICE FOR DELIVERING MATERIAL TO AN EYE

(75) Inventors: Daryl E. Anderson, Corvallis, OR (US); Andrew L. Van Brocklin, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 410 days.

(21) Appl. No.: 10/412,057

(22) Filed: Apr. 10, 2003

(65) Prior Publication Data

US 2004/0204674 A1  Oct. 14, 2004

(51) Int. Cl.
*A61M 31/00* (2006.01)

(52) U.S. Cl. .......................... 604/66; 604/521

(58) Field of Classification Search ........... 604/65–67, 604/521; 607/62
See application file for complete search history.

(56) References Cited

U.S. PATENT DOCUMENTS

| | | | |
|---|---|---|---|
| 4,012,798 A | 3/1977 | Liautaub | |
| 5,152,435 A | 10/1992 | Stand et al. | |
| 5,265,288 A | 11/1993 | Allison | |
| 5,588,564 A | 12/1996 | Hutson et al. | |
| 5,630,793 A | 5/1997 | Rowe | |
| 5,807,357 A | 9/1998 | Kang | |
| 5,881,956 A | 3/1999 | Cohen et al. | |
| 5,997,518 A | 12/1999 | Laibovitz et al. | |
| 6,159,188 A | 12/2000 | Laibovitz et al. | |
| 6,203,759 B1 | 3/2001 | Pelc et al. | |
| 6,216,966 B1 | 4/2001 | Prendergast et al. | |
| 6,398,766 B1 | 6/2002 | Branch | |
| 6,422,431 B2 | 7/2002 | Pelc | |
| 6,885,818 B2 * | 4/2005 | Goldstein | 396/59 |

* cited by examiner

*Primary Examiner*—Catherine S. Williams

(57) ABSTRACT

A method and device for administering material to an eye during an eye-open interval. The device includes, an electronically controllable fluid delivery element and a detector in communication with the electronically controllable fluid delivery element. The detector is capable of discerning at least a portion of an eye-blink event and producing a signal actionable on the electronically controllable fluid delivery element.

49 Claims, 8 Drawing Sheets

DISPENSING METHOD AND DEVICE FOR DELIVERING MATERIAL TO AN EYE

BACKGROUND OF THE INVENTION

This disclosure is directed to ophthalmic dispensing devices which can deliver various fluid materials such as gases and/or therapeutic liquids into contact with appropriate optic tissue. The disclosure is also directed to a method for administering a suitable material into contact with optic tissue.

Ophthalmic dispensing devices have been employed to administer various therapeutic fluids into contact with optic tissue including, but not limited to, the sclera, cornea, conjunctiva, and the like. Examples of such devices include eye spray devices, eyedroppers, eye wash units, and the like. Additionally, various ophthalmic devices have been proposed which administer gaseous materials into contact with the eye. Examples of such devices include devices that measure interocular physical characteristics of the eye such as pressure pupil dilation, etc.

The efficacy and ease of use for ophthalmic devices depends in part on the eye-blink response of the individual. Significant or uncontrolled eye-blink response can compromise administration effectiveness of devices dispensing materials such as therapeutic fluids or gasses. Additionally, exaggerated or uncontrolled eye-blink responses can make examination for conditions such as interocular pressure extremely stressful and uncomfortable for the patient. Devices that would increase administration accuracy and/or comfort relative to eye-blink response would be highly desirable.

SUMMARY OF THE INVENTION

Disclosed is a device and method for administering a fluid material to the eye utilizing an electronically controllable fluid delivery element. The device and method also include a detector in communication with the electronically controllable fluid delivery element. The detector is capable of discerning at least one portion of an eye-blink cycle and producing a signal actionable on the electronically fluid element.

DETAILED DESCRIPTION OF EMBODIMENTS

Figure 1:
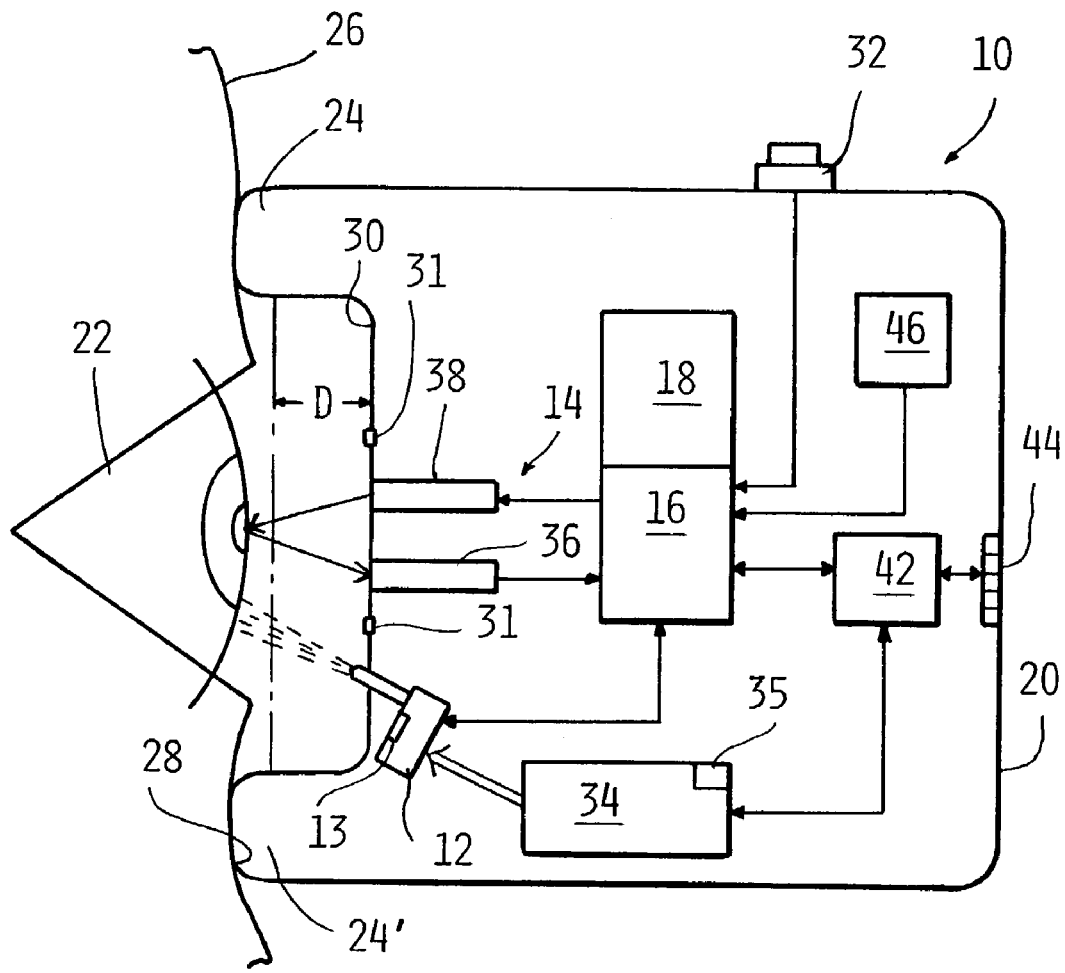
FIG. 1 is a schematic representation of an embodiment of an ophthalmic dispensing device as disclosed herein.

Disclosed is an ophthalmic dispensing device configured to which deliver discrete quantities of material into contact with the eye during the eye-open portion of the eye-blink cycle. The material administered and delivered into contact with the eye is a material suitable for use in association with optic tissue. The material is generally one that is appropriate or useful in various therapeutic and/or diagnostic applications.

The material may be any fluid or fluidizable material. Generally such materials are liquids, gasses, or mixtures of the two. Thus, the material employed and delivered is one that may be administered as liquid droplets, as liquid entrained in gas, or as a gaseous material. Examples of gaseously administered material include dosages of gasses administered into contact with the eye to ascertain interocular pressure and the like.

Nonexclusive examples of classes of therapeutic liquid material that may be employed for ophthalmic use include, but are not limited to, cholinergics agonists, alpha-adrenergic agonists, beta-adrenergic receptor antagonists, mydriatic materials, cycloplegics, corticosteroids, and prostaglandins. Examples of cholinergics or parasymptomimetic drugs include, but are not limited to, pilocarpine, acetylcholine, and carbachol. Examples of adrenergic agonists include, but are not limited, to epinephrine, dipivefrin, clonidine, apraclonidine, and brimonidine. Examples of beta-adrenergic antagonists or blockers include, but are not limited to, timololmaliate, timololhemihydrate, levobunolol, carteolol, metipranolol, and betaxolol.

Additionally, it is contemplated that materials such as topical carbonic anhydrase inhibitors can be administered. Examples of these include, but are not limited to dorzolamide and benzolamide. Examples of prostaglandin analogues and related derivatives include, but are not limited to, latanaprost, various ocular hypotensive lipids, unoprostone, various leukotrienes as well as antagonists of prostaglandins and leukotrienes.

It is also contemplated that other therapeutic materials can be administered using the device and method as disclosed. These include materials such calcium channel blockers, anti-inflammatory compounds, antimicrobials, immunomodulators, growth factors, hormones, cytokines, anesthetics, diagnostic agents, as well as artificial tears and viscosifying agents. Examples of mydriatics and cycloplegics include, but are not limited to, phenylephrine, tropicamide, atropine, and cycloplentalate.

Anti-inflammatory compounds include, but are not limited to, materials such as dyclofenac, ketorolac, dexymethisone, fleuromethelone, prednisolone, and loteprednol. Examples of antimicrobials include, but are not limited to cyprofloxacin, oxfloxacin, and triflurthymide. Examples of immunomodulators and various wound healing modulators include, but are not limited to, Motomsin C., V-Flurouracil, and cyclosporine.

Various growth factors that can be administered interocularly include, but are not limited to, EGF, DDNF, FEGF, and FGF. Examples of hormones that can be ocularly administered include, but are not limited to, certain growth hormones, glucagons, and insulin. Examples of cytokines that can be interocularly administered include TNF and interleukines.

It is also contemplated that the device and method as disclosed include, but not be limited to, materials such as proparacaine and tetracaine. Examples of diagnostic agents capable of administration by the method and device include, but are not limited to, materials such lycamine agents, rose bengal and flouroscein. The various agents can be employed to produce artificial tears or appropriate viscosification. These include, but are not limited to, materials such as carboxymethylcellulose, polyvinyl alcohol, hydroxymethylcellulose, and polycarbophil.

As used herein, the term "optic tissue" is taken to include structures associated with the eye. Structures associated with the eye include, but are not limited to, the iris, pupil, and sclera as well as connective tissue and overlying cellular layers and the like such as conjunctiva which overlays the eye structures previously mentioned. The term "tissue" is taken to mean an aggregate of cells taken together with their intercellular substance that form anatomical structure such as the conjunctiva, pupil, or the like.

The eye to be treated is typically one covered by musculature that defines eyelid(s) that retractably cover the anterior portion of the eye, including the cornea, iris, sclera and the like. The eyelid(s) cycle between a state in which the anterior portion of the eye is at least partially covered and a state in which the anterior portion is at least partially exposed is referred to herein as "eye-blink cycle" or "eye-blink event." The eye-blink cycle serves to protect the associated eye and to insure that the eye receives hydration, oxygenation and cleansing typically through tears or secretions produced by associated lachrymal glands. The eye-blink cycle serves to distribute tears over the surface of the associated eye. In most species with retractable eyelid structures, the eye-blink cycle is an autonomic or reflex response that can be partially overridden by independent higher order voluntary control. Thus the eye-blink event is under partial control of the individual but includes a significant reflexive response component. While the discussion relating to the disclosure is directed primarily to administration of material to the eyes of humans, it is also considered within the purview of this invention that the device and method could be employed to administer material to other species including, but not limited to, various other mammalian species, avian species and reptilian species.

It is to be noted that as used in the specification in the appended claims, the singular forms of "a", "an", and "the" include plural referents unless the context clearly dictates otherwise.

Referring now to FIG. 1, an ophthalmic dispensing device 10 is disclosed which includes an electronically controllable fluid delivery element 12 and a detector 14. The detector 14 and electronically controllable fluid delivery element 12 are in electronic communication with control electronics 16. Control electronics may include a suitable information storage portion 18.

The dispensing device 10 can also include a suitably configured housing 20 in which the various components such as the electronically controllable fluid delivery element 12 and detector 14 can be positioned. As depicted in FIG. 1, the housing 20 can be configured to facilitate its locatable positioning relative to eye 22 to permit administration of a material by the electronically controllable fluid delivery element 12. The housing 20 can include at least one appropriately positioned orientation surface such as projection(s) 24, 24' adapted to contact external anatomical surfaces surrounding the eye 22. The orientation surface can be configured to maintain the device 10 in a suitable spaced relationship relative to the anterior portion of the eye 22. The orientation surface can be configured to releasably contact anatomical regions proximate to the eye 22.

As depicted in FIG. 1, an upper projection 24 contacts the anatomical region above the eye 22. The contacted anatomical region above eye 22 is generally located on the forehead 26 of the user and may be in the region proximate to the opening defining the optic orbit. A corresponding lower projection 24 can contact a region below the eye 22 such as the upper cheek region 28 generally proximate to the region defining the lower orbit. The projection(s) 24, 24' may be configured to assist in orienting the device 10 relative to the eye 22. Thus the projection(s) can be contoured to correspond to a position or positions of the facial region surrounding the optic orbit. If desired, the projection(s) 24, 24' can be configured to screen the associated eye 22 from external light, air movement or the like.

The housing 20 of device 10 can also include a suitable surface 30 adapted to be located a spaced distance D from eye 22 when the device 10 is in the use position. The spaced distance D is one which will permit unimpeded eye-lid movement during eye-blink events. The spaced distance D will also permit introduction of material and effective detection of the eye-open state. The surface 30 may have any suitable surface contour or geometry. The surface 30 may have suitable access apertures for transmission of material from associated electronically controllable fluid delivery elements 12 and for operation of suitable detector(s) 14. The surface 30 may also include suitable orientation indicia that can facilitate positioning of the device 10 for effective operation. These can include visually discernable indicia such as markers 31 as well as cross hairs, etc.

The dispensing device 10 as depicted in FIG. 1 also includes a suitable trigger mechanism 32 that is configured to permit activation of the device 10. As depicted in FIG. 1, the trigger mechanism 32 is in communication with the control electronics 16, associated detector 14 and electronically controllable fluid delivery element 12 to accomplish actuation of the device 10. As depicted in FIG. 1, the trigger mechanism 32 is a button positioned on the exterior surface of housing 20 in electronic communication with control electronics 16. Other mechanical, electrical or electromechanical devices can be employed as a trigger mechanism as desired or required. It is contemplated that the trigger mechanism can be employed as a sole activation mechanism or in combination with other devices and mechanisms, which can include, but are not limited to, touch sensors, proximity sensors or the like that can ascertain whether the device 10 is in position and ready to deliver the desired material.

The dispensing device 10 as depicted in FIG. 1 also includes a suitable reservoir 34 in fluid communication with the electronic fluid delivery element 12. The reservoir 34 contains one or more materials suitable for contact with optic tissue. Such materials may have efficacy as therapeutic agents, diagnostic agents, palliatives or carriers for treatment of conditions associated with the eye or can be capable of uptake by optic tissue for treatment of systemic conditions. The material may be any fluidizable compound or combination of compounds. Materials may be gaseous or liquid as well as combinations of the two. It is also contemplated that, where appropriate, optically compatible solids may be administered. Such solids may be materials appropriate for optic administration. Such materials may be sized at or below near-microscopic or microscopic level and may include, but not be limited to, digital diagnostic media, sampling media and the like that would be biodegradable and/or biocompatible.

The electronically controllable fluid delivery element 12 may be a suitable microfluidic device capable of producing or emitting aerosolized material in a size range and velocity that facilitates introduction into the eye. Examples of such devices include, but are not limited to, electronically controllable jetting devices that may incorporate control and structural features commonly associated with ink jet printing devices. Electronically controllable jetting devices include, but are not limited to, piezoelectric devices, thermal fluid devices, and vibrating membrane devices with piezoelectric actuators capable of dispensing material upon receipt of an activation command.

The device 10 may include temperature regulator(s) to control the temperature of the material before administration or during administration. The electronically controllable fluid delivery element 12 may also include suitable temperature regulator(s) 13 and 35 which will maintain the temperature of the administered material in a temperature range which facilitates material uptake on the optic tissue and/or minimizes user perception or discomfort upon material administration. The storage reservoir 34 may also include suitable temperature regulator(s) 35 which can control the temperature of the stored material. The storage reservoir regulators 35 may maintain a material temperature in a range that facilitates optic tissue uptake and/or user comfort. Alternately, temperature regulator 35 can be employed to maintain contents of storage reservoir 34 at a temperature that maintains material potency, etc. The regulators 13, 35 may be used independent of one another or in concert as desired or required.

Control electronics 16 can be any suitable logic-processing unit that can be maintained in electronic communication with the electronically controllable fluid delivery device 12 and the detector 14. Control electronics 16 may be any configuration of hardware and/or software maintaining logic and circuitry capable of interactive function with the electronically controllable fluid delivery device 12 and the detector 14. Suitable control electronics 16 can be capable of interactive communication and control with the electronically controllable fluid delivery device 12 as well as receiving input from various internal and external sources and devices which may include the detector 14, trigger mechanism 32, and user interface 42. Control electronics 16 can include suitable device(s) and/or logic configured to mediate signals received from the detector 14 as well as information or data derived from other sources and generate suitable actions such as commands actionable on the electronically controllable fluid delivery element 12.

It is contemplated that control electronics 16 can be configured or programmed to resolve data obtained through one or more eye-blink cycles in order to generate an appropriate activation and deactivation sequence for the electronically controllable fluid delivery element 12 to introduce the desired fluid material into the eye 22 during the eye-open portion of the eye-blink cycle. It is also contemplated that control electronics 16 can perform and regulate various tasks related to the operation of device 10 which can include, but which are not limited to, programming tasks and activities as well as signal processing tasks and activities. Control electronics 16 can be configured or programmed to perform the desired operational and signal processing functions and include such configurations as found in central processing units and/or application processing units.

As depicted in FIG. 1, control electronics 16 can be configured with a suitable information storage portion 18. Information maintained in the information storage portion 18 may include, but is not limited to, information regarding dosing parameters, dose administration intervals, drug interactions, dosage look up tables, optic topographic data and look up tables, and the like. It is also contemplated that the information storage portion 18 may include information relevant to signal boundaries or other information relevant to interpreting and processing signal inputs from various sources, such as detector 14.

Detector 14 is a device capable of discerning or detecting a physical change associated with the eye-blink event and, more particularly, with the eye-open state. The physical change discerned or detected can be any characteristic including, but not limited to, changes in reflected light and changes in reflected sound.

In the device 10 as disclosed; the detector 14 may be configured to produce a signal which can be transmitted to appropriate elements such as an application specific integrated circuit or other suitable processing element associated with control electronics 16. It is also contemplated that the detector 14 can be configured to generate higher order data as desired or required to determine optimum administration intervals and/or administer material during at least one eye open state.

The detector 14 is configured to detect exposure of the optic tissue during the eye-blink event. The detector 14 may include any suitable sensor device 36 capable of detecting at least one characteristic of an eye-blink event. The characteristic may be one that is associated with an eye-open state. The sensor device 38 may be configured to detect gradations or degrees of change between the eye-open state and the eye-closed state and, in concert with control electronics 16 or other elements in the device 10, determine a threshold level for eye-open and/or eye-closed states for activation of the fluid delivery element 12.

Detection can be taken to mean gross recognition of a structure located in the anterior region of the eye such as the pupil. Detection can also include registration and recognition of changes within an observed structure such as pupil dilation and constriction. Detection may also include registration and recognition of transformation(s) in structure(s) or in localized or generated transformation in topography or contour of a structure due to perturbation or traumatic assault.

The detector 14, working in concert with any suitable control electronics 16, may be one which is capable of implementing a suitable detection and recognition strategy. The detection and recognition strategy may be any strategy that can adequately register and recognize an eye-open state or specified structural changes. As employed herein, the term "eye-open state" is defined as a condition in which at least one of the upper and lower eyelids is at least partially retracted leaving at least a portion of the anterior segment of the eye exposed. It is contemplated that the eye-open state will be one in which at least a portion of the pupil is visible.

Detection and recognition of the eye-open state in the device 10 as disclosed in FIG. 1 may be accomplished by a method or protocol that detects the visible pupil. More particularly, detection and registration of the eye-open state is accomplished by the registration of detectable differences between the eye-open state and the eye-closed state by detector 14, either independently or in conjunction with associated control electronics 16. In the device 10 as disclosed herein detection and recognition occur in a manner which does not involve direct physical contact between the device 10 and the anterior portion of the eye 22.

As particularly disclosed herein, the eye-open state is ascertained by discernment of a measurable difference in a characteristic or characteristics associated with the eye-open state and the eye-closed state. The characteristic difference can be one that is inherently measurable or one that is developed by the production of a suitable analytic waveform and detection of at least a portion of the analytic waveform as reflected from a selected surface associated with the eye 22. The analytic waveform may be any suitable waveform that can be generated and directed toward optic tissue. It is contemplated that the analytic waveform may be an optical waveform having a wavelength or lengths in the visible and/or invisible spectrum. The detectable reflected waveform may be in the wavelength generated or may undergo suitable frequency translation based upon conditions which include, but are not limited to, characteristic(s) of the optic tissue, compounds or conditions present in the optic tissue, as well as compounds or materials introduced into the optic tissue by the device 10 or by other means. It is also contemplated that the analytic waveform may be of a type which produces a localized, distant or generalized perturbation in optic tissue that would be detectable by suitable optic detection devices. Such analytic waveforms can have optical and/or acoustic characteristics depending upon the type and manner of detection of the reflected waveform desired or required.

Figure 2:
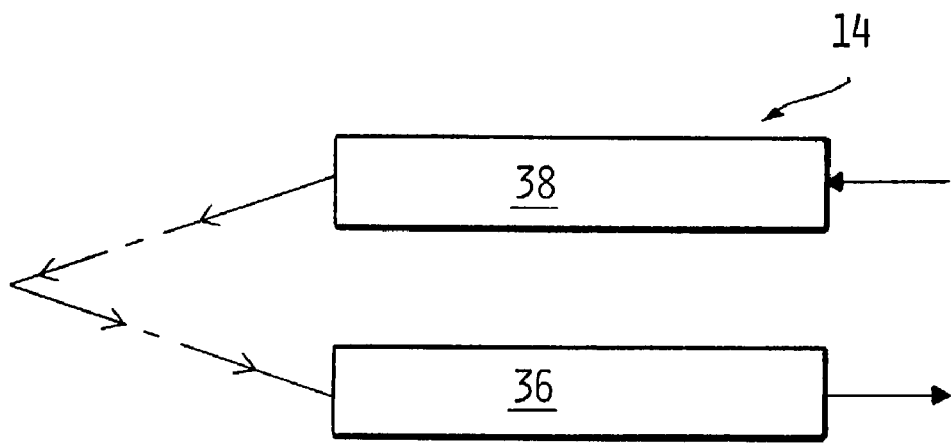
FIG. 2 is a detail drawing of FIG. 1.

As depicted in FIGS. 1 and 2, the detector 14 includes both a sensor 36 and an emitter 38. The emitter 38 can be a device that can produce a suitable analytical waveform compatible with the selected or targeted region of the anterior section of the eye 22. The emitter 38 can be an acoustical emitting device, a light emitting device, etc. In the dispensing device 10 as depicted, it is contemplated that the emitter 38 is a suitable light emitting diode calibrated to produce a focused beam of light directed at a suitable region of optic tissue such as the pupil. The type of analytical waveform and energy level at which the waveform is emitted is one that is determined to be appropriate and safe for use with the eye 22 and associated tissue such as eyelids.

The emitter 38 may be capable of continuous function or may be activated upon receipt of a suitable command signal. The command signal may be produced by any suitable triggering device such as trigger mechanism 32. The command signal may be received directly from the triggering device or can be mediated through control electronics 16. As depicted in FIG. 1, trigger 32 is a user-actuated switching mechanism. However, it is also contemplated that a triggering device can be configured as a proximity device or a touch pad device configured to produce an activation command upon contact with the anatomical region contiguous with the eye socket. It is also contemplated that the mechanical device 32 can interactively function with various proximity devices or touch pad devices as appropriate.

In the detector 14 as disclosed, the sensor 36 is capable of detecting exposure of the targeted optic tissue. It is contemplated that the detection can be an actual discernment reading or can be correlated from a change in at least one detectable characteristic based upon the exposure or non-exposure of the targeted optic structure such as the pupil. Where exposure or non-exposure is derived from a detected change in at least one characteristic associated with the targeted structure, it is contemplated that the sensor 36 will be one capable of detecting a waveform such as an optical waveform or acoustical waveform reflected from the eye structure and/or associated overlying eyelid(s). While waveform may be naturally occurring, in the device 10 as disclosed, the analytic waveform is one that is produced and emanates from emitter 38. It is contemplated that the sensor 36 will be calibrated to detect at least a portion of the reflected wave initially generated by the emitter 38.

The sensor 36 can be configured to produce a signal that is received by the control electronics 16 to generate a command actionable on the electronically controllable fluid delivery element 12. It is contemplated that the command actionable on the electronically controllable fluid delivery element 12 can be a firing command or a cease-fire command based upon the information provided from detector 14.

As disclosed in FIGS. 1 and 2, the device 10 is configured to ascertain exposure of at least a portion of the anterior portion of the eye 22 during the eye-blink event. Thus, the emitter 38 can generate an analytic waveform such as a narrow beam of light from a suitable light emitting diode directed toward a suitable optic structure located in the anterior portion of the eye 22. While the pupil is discussed as a specific example of such optic structure, it is contemplated that the targeted structure can be any suitable optic structure or region for which a detectable characteristic change relative to an eye-blink event can be detected through reflection of a portion of the analytic waveform back to a sensor 36 to ascertain detectable difference(s) in the characteristic under analysis.

The analytic waveform may be directed toward the eye 22 at any suitable angle. As depicted in FIGS. 1 and 2, the analytic waveform is directed toward the pupil region of the eye 22 at an angle generally perpendicular to the cornea tissue. When the analytic waveform is directed at the pupil in generally perpendicular orientation, at least a portion of the analytic waveform may be directed through the pupil to the retina. Thus the degree of reflectance may be affected by pupil dilation. It is contemplated that suitable detection routines can account for changes in pupil dilation either by correcting for variations or utilizing such detected changes to alter or adjust the material ejection patterns. The analytical waveform may be directed toward the eye at other angular orientations depending on various factors which include, but are not limited to, the nature of the optic structure targeted, the sensitivity of various eye structures to the analytic waveform being employed, and the like. Thus the emitter 38 may be positioned at any orientation capable of achieving an appropriate angle of incidence between the optic tissue and the analytic waveform.

It is also contemplated that the emitter 38 can be configured to produce multiple analytic waveforms of the same or varying types, at various wavelengths, at the same or varying angles of incidence to accumulate information regarding the eye-blink event and/or perturbation, stimulus response, medicinal uptake effect, and the like. Emitter 38 can include multiple waveform generators located and oriented as desired that provide reflected waveform information discernable by one or more sensor devices 36.

The eye-blink event results in the covering of the optic tissue with the associated eyelid. This results in a disruption or change in the reflection in emitted light that can be detected as a change in reflectance. This change in reflectance can be detected and expressed as a signal that can be conveyed to the control electronics 16 and associated information storage portion 18 where a value such as the rate of change of reflectance can be calculated to ascertain subsequent eye-open intervals.

The analytic waveform emitter such as a light emitting diode can be targeted at any appropriate portion or region of the optic tissue. As depicted in FIG. 1, the pupil is targeted to provide a significant degree in the change in reflectivity between the eye-open and eye-closed portions of the eye-blink cycle. Other locations can be targeted as desired or required. Such locations include, but are not limited to localized regions of perturbation as may occur in the sclera, regions of suspected injury and the like.

As depicted in FIG. 1, the detector 14 is positioned relative to interior surface 30 of housing 20 such that the detector 14 can be positioned relative to the desired optic structure to be targeted, in the device as illustrated, the detector 14 is located at a position opposed to the pupil region of the eye 22. The electronically controllable fluid delivery element 12 may be positioned in the housing 20 of device 10 in any location which will permit the ejection of material from element 12 and delivery of material to the eye 22. The position of the electronically controllable delivery element 12 will generally be one that maximizes the material delivery interval. The material delivery interval is defined by the interval during which the delivery region of the eye 22 is exposed. As depicted in FIG. 1, the electronically controllable material delivery element 12 is located in the surface 30 of the device at a position which will target a delivery region in the lower quadrant of the eye 22 between the edge of the lower lid and the pupil region. In typical human eye structures this will maximize the delivery interval by permitting introduction of material while the eye is open and during the initial phases of the lid closure portion of the eye-blink event. Additionally, targeting a delivery region in the lower quadrant of the eye 22 permits efficient administration of the material in a manner comfortable to the patient and efficient in material administration. The delivery region may be any portion of the eye 22 suitable for receiving the material to be delivered. Generally eye regions that are out of the direct visual field will be desirable to minimize user perception of the material being delivered.

The material can be administered as small droplets from one or more electronically controllable fluid delivery elements 12 which are activated concurrent with the eye-open portion of the eye-blink event and are deactivated as the eyelid(s) cover the delivery region during the eye-closed portion of the eye-blink event. Deactivation can occur upon receipt of a deactivation command triggered by indication of an eye-closed interval such as by the detection of a change in at least one characteristic associated with the onset of an eye-closed event. As disclosed herein the characteristic change is a change in detected reflectance. Upon registration of a change in detected reflectance, the electronically controllable fluid delivery element(s) 12 can be deactivated until reacquisition of the optic structure targeted by detector 14.

It is contemplated that the material can be administered over one eye-blink cycle or over multiple eye-blink cycles. Acquisition or reacquisition of the optic structure targeted by detector 14 results in a signal that can be mediated by control electronics 16 to produce a command to activate the electronically controllable fluid delivery element(s) 12 and to commence or resume administration of the desired material. Cyclic deactivation and reactivation of the electronically controllable fluid delivery element(s) can proceed until the desired dosage has been delivered. It is contemplated that the amount of material introduced into contact with the eye 22 in each eye-blink cycle can be adjusted to minimize user perception of and discomfort encountered with the introduction of the administered material.

It is also contemplated that the cyclic deactivation and reactivation can proceed in a manner that minimizes "flooding" due to fluid overload of the eye surface. Flooding can be perceived by the user as blurred vision. Flooding and other discomforts associated with introduction of material can trigger reflexes that result in production of excess tears. Excess tear production can have the adverse effect of diluting or removing the material administered.

In order to minimize user perception of administration, discomfort and/or flooding, the detector 14 may be calibrated to ascertain at least one response associated with user perception, discomfort, and/or flooding. To register flooding or tissue surface overload, the detector can be configured with a suitable emitter and sensor capable of registering changes in surface fluid levels. To register user perception and/or discomfort, the detector can be configured to register signature changes on optic tissue or eye-blink response generally associated with perception and/or discomfort. Once one of these situations is registered, suitable commands can be generated by control electronics to address and mitigate the situation.

Where material is administered through multiple eye-blink events, the detector 14 may be configured and calibrated to ascertain optic surface fluid levels and produce suitable signals regarding such information which can be mediated by suitable control circuitry as may be present in control electronics 16 to regulate the action of electronically controllable fluid delivery element(s) 12.

Where material is administered through multiple eye-blink events, it control electronics 16 can also include appropriate logic to determine proper dosage and to issue a proper command to override information or signals produced by detector 14 and terminate function of the electronically controllable fluid delivery element(s) 12. If desired, the control electronics 16 can also provide an appropriate signal to the user that the dose has been administered.

It is also contemplated that a material can be administered through multiple electronically controllable fluid delivery elements directed at various regions of the eye 22. Additionally, it is contemplated that various electronically controllable fluid delivery elements can provide different materials in suitable combination(s) or sequences. Suitable combinations can administered concurrently or sequentially depending on at least one of the materials, nature of the dosing requirements, treatment regimens, and the like. It is contemplated that factors such as combinations of materials administered, amounts of materials administered and/or administration intervals can be controlled by any suitable command protocols resident in the device 10. Such command protocols can be determined by information contained in the control electronics or can be externally programmed or implemented in any suitable fashion.

As depicted in FIG. 1, device 10 also includes a suitable user interface 42 in electronic communication with control electronics 16. The user interface 42 is configured to permit communication and interaction with external sources. External sources can include, but need not be limited to, the user or appropriate medical personnel directly or indirectly as well as externally positioned logic and data acquisition devices.

Where the interface 42 is in communication with the user or medical personnel, the interface 42 can include suitable input mechanisms and readout devices such as keypads, electronic displays, and the like. Where the interface 42 is in communication with external electronic communication and data acquisition devices, interface 42 may include or be in communication with a suitable port 44 to facilitate wired or wireless communication with an external source. Ports 44 may be configured to permit infrared digital communication, wired or wireless telecommunications, etc. Communications can include any suitable transfer of data and information including, but not limited to, download of information stored in the device, upload of information pertaining to material type, dosing, parameters, optic conditions, etc.

The device 10 may also include an appropriate chronometric element 46 to determine such factors as dosage interval, uptake interval, and the like. In the device 10 as depicted in FIG. 1, the chronometric element is in electronic communication with control electronics 16.

The chronometric element 46 can function in concert with control electronics 16 to permit data acquisition surrounding each dose administration. The data include, but are not limited to, date and time, dosage volume, and dose response. Such data can be maintained in appropriate data storage elements either on board the device 10 such as in the information storage portion 18, or in suitable external data storage devices. Information derived from chronometric element 46 and associated devices and elements can be employed to provide a suitable lockout or override system to regulate dosage administration. Stored information can be accessed and transferred or manipulated as desired or required utilizing the user interface 42 and linking port 44.

Figure 3A:
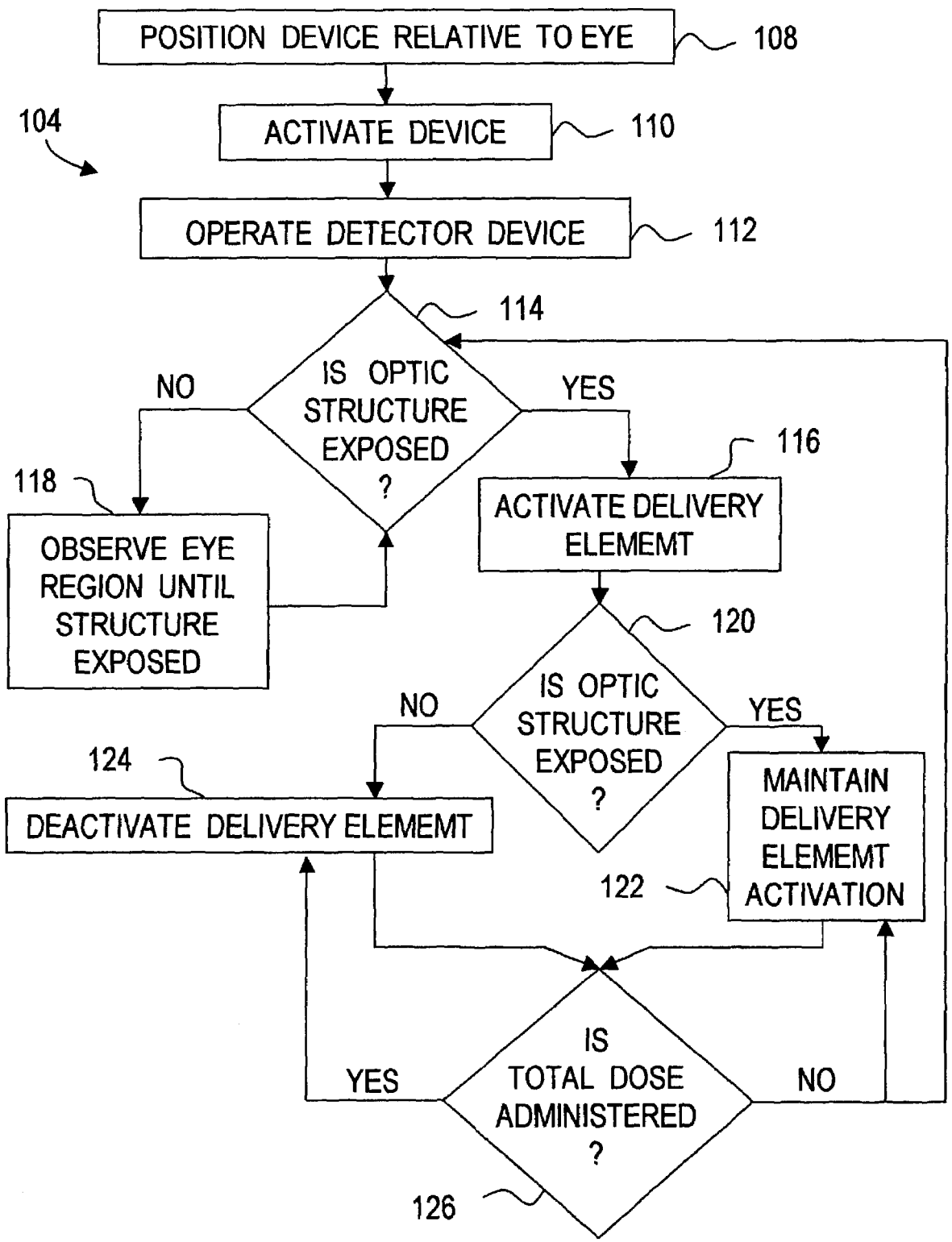
FIG. 3A is a process diagram of a method for administering material to optic tissue according to an alternate embodiment as disclosed herein.

A method 104 of dosage administration is schematically illustrated in FIG. 3A. The device 10 is positioned relative to the eye 22 as at reference numeral 108. Proper positioning can be determined by location of projections 24, 24' relative to the upper and lower orbital cavity. It is contemplated that proper positioning may be ascertained by other suitable targeting aids which could include an orientation tool such as an appropriate light beam relative to a targeted optic structure or the like.

Once the device 10 is in position relative to eye 22, the device can be activated as at reference numeral 110 and the detector 14 can be activated and operated, as at reference 112. Operation or initiation of the detector 14 can be by any suitable means. In the device 10 as set forth in FIG. 1, a trigger 32 can initiate operation of the detection device, for example by production of a suitable analytical waveform from the emitter 36 such as a beam of light produced by a suitable light emitting diode.

In the process as outlined in FIG. 3A, acquisition of the targeted optic structure is determined at decision point 114. Acquisition of the targeted optic structure indicates that the option structure is exposed. Exposure of the optic structure can be determined by any suitable means. In the device set forth in FIG. 1, sensor 36 of detector 14 is employed to detect reflected light and to characterize the reflectance as indicative of the eye-open or eye-closed state. Ascertainment of eye-open state and/or eye-closed state is determined after suitable reflectance analysis.

Positive acquisition of the targeted optic structure triggers the activation of the electronically controllable fluid delivery device 12 as at reference numeral 116. If optic structure is not detected and/or acquired, the eye is observed until the targeted structure is exposed and acquired as at reference numeral 118. When the targeted optic structure is detected, the fluid delivery element is activated. The analysis for exposure of optic structure continues after fluid delivery element activation as at reference numeral 120. Continued exposure of the optic structure results in continued delivery activity as at reference numeral 122. Interruption in detection of the due to either removal of the device 10 from position relative to the eye 22 or the extension of the eyelid(s) over the targeted region of the eye 22 results in deactivation of the fluid delivery element as at reference numeral 124. Once the total dose is administered as at 126, a signal is produced to override detection-based control of the fluid delivery element and deactivate the fluid delivery element. Where appropriate, the detection activity may continue subsequent to deactivation of the fluid delivery element to observe or confirm material uptake, or to observe optic tissue response.

It is contemplated that the electronically controllable fluid delivery element(s) can be configured to administer a droplet or series of droplets in a manner that will facilitate uptake in the eye. The velocity, volume, and/or temperature of the given droplets can be adjusted to increase user comfort or to minimize user material administration. If necessary, the material can be administered over a number of eye-blink events to provide total dosage administration and to facilitate uptake in the optic tissue.

Figure 3B:
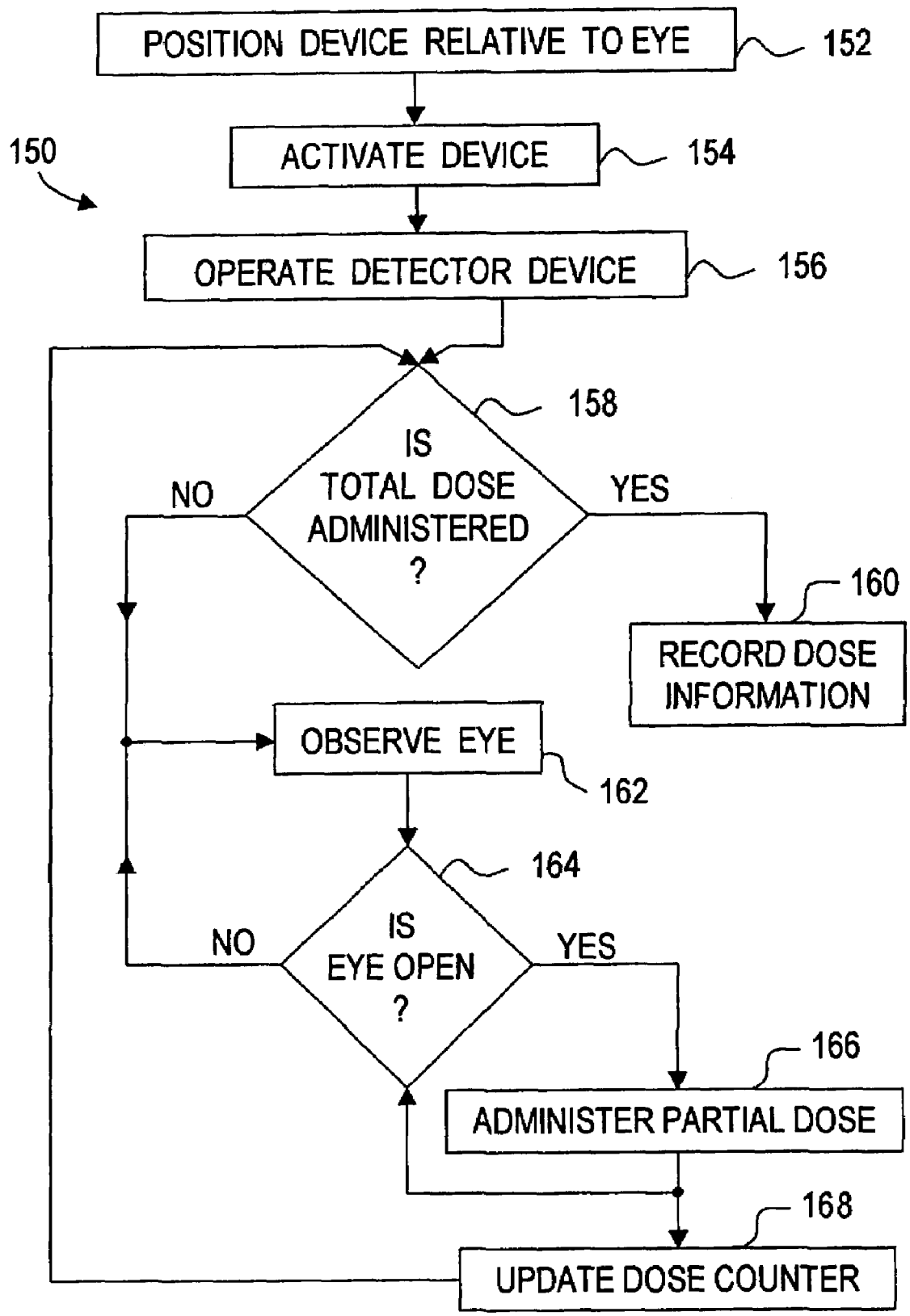
FIG. 3B is a process diagram of a method for administering material to optic tissue according to an alternate embodiment as disclosed herein.

A method 150 of dosage administration is schematically illustrated at FIG. 3B. In this alternate method 150, the device 10 can be positioned relative to the eye 22 as at reference numeral 152. Proper position can be determined by location of projections 24, 24' relative to the upper and lower orbital cavity and by utilization of markers 31.

Once device 10 is in position relative to eye 22, the device 10 can be activated as at reference numeral 154, and detector 14 can be activated and operated as at reference numeral 156. Operation or initiation of the detector 14 can be by any suitable means. In the device as set forth in FIG. 1, the operation of the detector device can be initiated by any suitable trigger or other event.

In the process as outlined in FIG. 3B, decision junction 158 determines whether total dose has been administered. If total dose has been administered, dosage information can be recorded as at reference numeral 160. If the total dose has not been administered, the eye is observed as at reference numeral 162 utilizing detector 14 to ascertain an eye-open state. The eye-open state is determined at decision junction 164. If the eye-open state is not determined, observation of the eye continues as at reference numeral 162 until the eye-open state is confirmed. Upon confirmation of the eye-open state, a partial dose of the material is administered as at reference numeral 166.

The partial dose can be any amount or volume that can be efficaciously delivered to the eye during an eye-open interval. Thus, the partial dose may be an amount capable of being ejected during one firing of one nozzle associated with an electronically controllable delivery device. The partial dose could also be a larger quantity depending upon the material, optic condition, etc. Thus, the partial dose can constitute one or more firing of one or more nozzles in a continuous or noncontinuous manner for an interval up to the occurrence of an adverse delivery event. As used herein, the term "adverse delivery event" is taken to mean undesirable events such as user discomfort, flooding, or the like. The interval contemplated herein is one that is considered short enough to permit efficient introduction of the material to the eye during the eye-open interval. Thus, the partial dose is ascertained by factors such as chronological interval and volume administration.

Once a proper partial dose has been administered, the dose counter is updated as at 168, and the system is queried to determine whether a total dose has been administered as at 158. Typically, positive indication that a total dose has been administered will occur when the dose counter is greater than or equal to a value determined to be the total dose. It is to be understood that total dose, partial dose, and other appropriate parameters can be ascertained by appropriate logic devices such as the control electronics. Furthermore, the particular characteristics of the partial dose administered can be varied, if desired, depending upon data received regarding eye-blink events, optic condition, and the like. Additionally, partial dose may be calculated or determined by other external factors.

It is contemplated that the iterative nature of the process depicted in FIG. 3B can permit effective and rapid administration of material over a series of eye-blink events.

Figure 4:
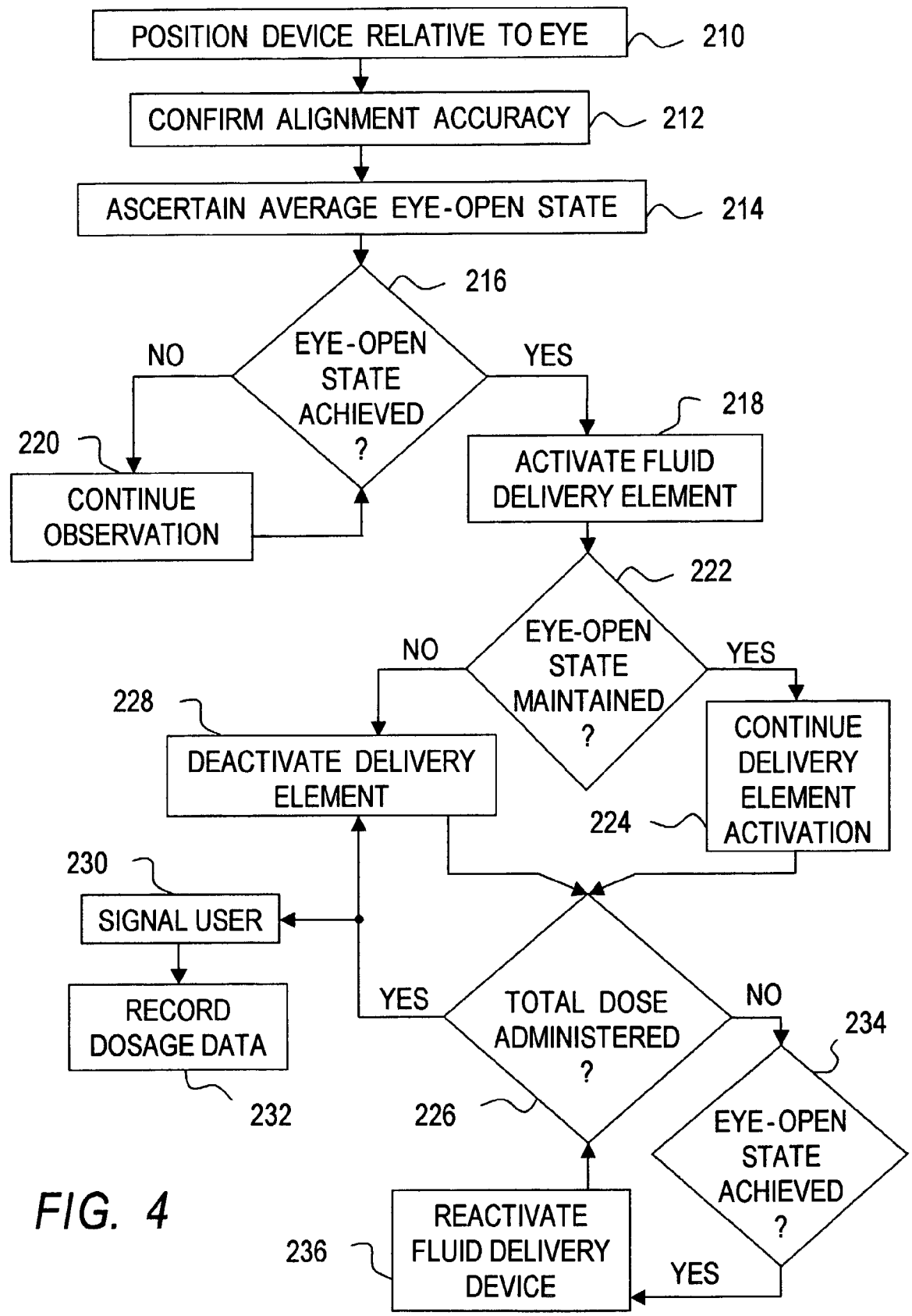
FIG. 4 is a process diagram of a method for administering material to optic tissue according to an alternate embodiment as disclosed herein.

A more detailed process for administering a material to the eye is outlined in FIG. 4. As depicted in FIG. 4, the device 10 can be positioned relative to the eye 22 as at reference numeral 210. Positioning can occur by any suitable mechanical and/or user-guided procedure. Alignment accuracy of the device 10 can be confirmed by appropriate physical guides and/or visual cues as at reference numeral 212. Examples of physical guides include the projections 24, 24' previously discussed. Visual cues can also include indicia such as cross hairs, parallax markers, or simply positional locator devices such as markings 31 present on surface 30 which the user can use to position the device locating the indicia relative to his or her visual field. It is also contemplated that alignment accuracy can be ascertained by suitable electronic assessment methods which can provide a suitable visual, audible or mechanistic confirmation of alignment accuracy. In situations where electronic devices are employed to ascertain accuracy, alignment accuracy may be an interactive process whereby alignment accuracy is electronically assessed and results in an audible or other externally discernable signal. It can be appreciated that an externally audible signal would be highly desirable in situations where the patient is unable to visually determine device placement and alignment accuracy due to age, lack of visual acuity, or other disabilities.

Once device placement and alignment accuracy have been confirmed, the typical or average eye-open interval or state can be ascertained as at reference numeral 214. As used herein, the term "eye-open state" is taken to mean the interval during the eye-blink cycle that the eyelids are retracted and at least a portion of the anterior portion of the eye is exposed. During the eye-open state material can be successfully administered to the optic tissue. In the method as disclosed, It is contemplated that assessment of the eye-open state will be accomplished over a plurality of eye-blink events to assemble an appropriate base of information regarding differences in at least one characteristic of the eye-open and eye-closed states in order to permit detection of subsequent eye-open intervals for administration of material.

Once sufficient data have been accumulated to define the eye-open state, recognition of an eye-open state as at reference numeral 216 by a suitable detector such as detector 14 can result in generation of a suitable signal or command which ultimately results in activation of the electronically controllable fluid delivery element 12 as at reference numeral 218. Failure to detect an eye-open state results in the continued analysis and observation of the eye 22 as at reference numeral 220.

Administration of material from the activated fluid delivery element can continue as long as the eye-open state is maintained as at decision junction 222. Thus it is contemplated that the detector such as detector 14 will continue to analyze the characteristic associated with the eye-open and eye-closed states of the eye-blink event to ascertain whether the eye remains in the eye-open state as at reference numeral 222. Continuation of the eye-open state can result in continued activation of the electronically controllable fluid delivery element as at reference numeral 224. The electronically controllable fluid delivery element can remain activated until total dosage is administered as at decision junction 226. Delivery of total dose can be ascertained by any suitable manner. For example, dosing information regarding total dosage, dosage interval, and the like can be maintained in suitable information components of the control electronics or in other appropriate on-board or externally maintained data storage device. It is contemplated that data regarding dosage administered can be derived in a direct manner from a volumetric measurement of the material administered as obtained from sensors associated with either reservoir 34 or jetting device 12. Alternately, it is contemplated that data regarding dose administration can be derived inferentially from information regarding actuation interval of the electronically controllable fluid delivery element and, in the case of electronically controllable jetting devices, knowledge of values such as nozzle firing data, firing chamber volumetric information, and the like.

Delivery of total dose as at decision junction 226 results in a command to deactivate the fluid delivery element as at reference numeral 228. When total dose has been administered, a suitable signal can be provided to the user as at reference numeral 230 and dosage data can be recorded as at reference numeral 232. Suitable signal or indication produced upon administration of the total dosage can be an audible or visual indication to the user that the dose has been administered. Such indication can include, but is not limited to, deactivation of any light-emitting diode employed in the detector array 14 and/or generation of an audible or visually detectable signal, as through an appropriate signal device.

Deactivation can also occur when the eye-open state is not maintained or registered as would occur during the eye-closed portion of the eye-blink event or when the device 10 is removed from position relative to the eye 22.

The method contemplates that the actuation of fluid delivery element and administration of material to the eye can be interrupted with each eye-blink event. Thus, when an eye-open state is not confirmed, the electronically controllable fluid delivery element is deactivated. Analysis of the eye-open state can continue subsequent to deactivation of the electronically controllable fluid delivery element. Thus, if total dose administration has not been achieved as at decision junction 226, a subsequent registration of an eye-open state as at junction 234 can result in reactivation of the electronically controllable fluid delivery element as at reference numeral 236. The process can be iteratively repeated until total dose has been administered.

Also disclosed is a method for administering material to an eye that includes a pupil and an eyelid. In the method disclosed, a device including an electronically controllable fluid delivery element is positioned in proximate alignment to the eye. As used herein, the term "proximate alignment" is defined as a position in spaced distance from the surface of the eye sufficient to permit the targeted delivery of a material from a suitable fluid delivery element into contact with the eye. The administration device positioned in proximate alignment to the eye includes at least one electronically controllable fluid delivery element as well as a detector capable of ascertaining eye-open state of the associated eye. The device also includes appropriate control electronics operable on the electronically controllable delivery element. The control electronics are capable of generating operation commands based upon data received from the detector.

In the method as broadly disclosed, the detector is actuated to ascertain an eye-open state of the associated eye once the device is in position. Fluid material is dispensed from the electronically controllable fluid delivery during the ascertained eye-open state. The material dispensed can be either a gaseous material and/or an appropriate therapeutic liquid.

A plurality of eye-blink events can be ascertained and analyzed to determine an average eye-open state. The plurality of eye-blink events are analyzed prior to the material dispensing step to provide an accurate definition of eye-open state. In order to accomplish eye-blink analysis, a waveform can be produced by an emitter portion of the detector and directed toward a targeted eye region. The reflected waveform is recorded by a suitable sensor and analyzed to define eye-open and eye-closed states. It is contemplated that the reflected waveform is analyzed over time to define an eye-blink event that includes at least one eye-open interval and at least one eye-closed interval to ascertain relative differences between the analytical waveform wave events during the two states. In the method as disclosed, the dispensing step is timed to occur during at least a portion of the eye-open state. The analytical waveform that is produced and directed toward the eye region may be any suitable waveform capable of reflection and recordation. Thus, various acoustic and/or optical waveforms can be employed.

As disclosed herein, the analytical waveform can be a beam of low energy light such as a direct beam emitted by low power light emitting diodes and the like. The waveform may be in the visible or invisible range. It is contemplated that where a visible light LED is employed, the light beam can also function as an alignment mechanism. For instance, the user can visually utilize the LED produced beam to provide proper alignment of the dispensing device relative to the eye.

It is contemplated the sensor can be an appropriate photodiode which is aimed at the eye and filtered to receive the specific wave length produced by the LED to detect the LED produced light reflected off the eyelid or eye surface region. It is contemplated that through several blink events, the photodiode would detect a reflectance waveform which can be processed by the control electronics and information storage unit to provide data regarding reflectance levels which represent the eye surface and the associated eye-open state and those which represent the eyelid and the associated eye-closed state.

Actuation of the electronically controllable fluid delivery element can occur after appropriate determination of reflectance levels for the eye-open state and the eye-closed state. After the levels have been determined, the user continues to blink. The detector 14, mediated by the associated control electronics 16, ascertains the next eye-open state. Upon occurrence of this event, a signal is transmitted and a command is generated that is actionable on the electronically controllable fluid delivery element to emit material and direct the delivery region of open eye. Activation of the electronically fluid delivery element devices continue until the dosage is complete or the eye-open detect is lost. If the dose is incomplete, the detector, in association with the control electronics, watches for the next eye-open state to continue administering the dose.

Figure 5:
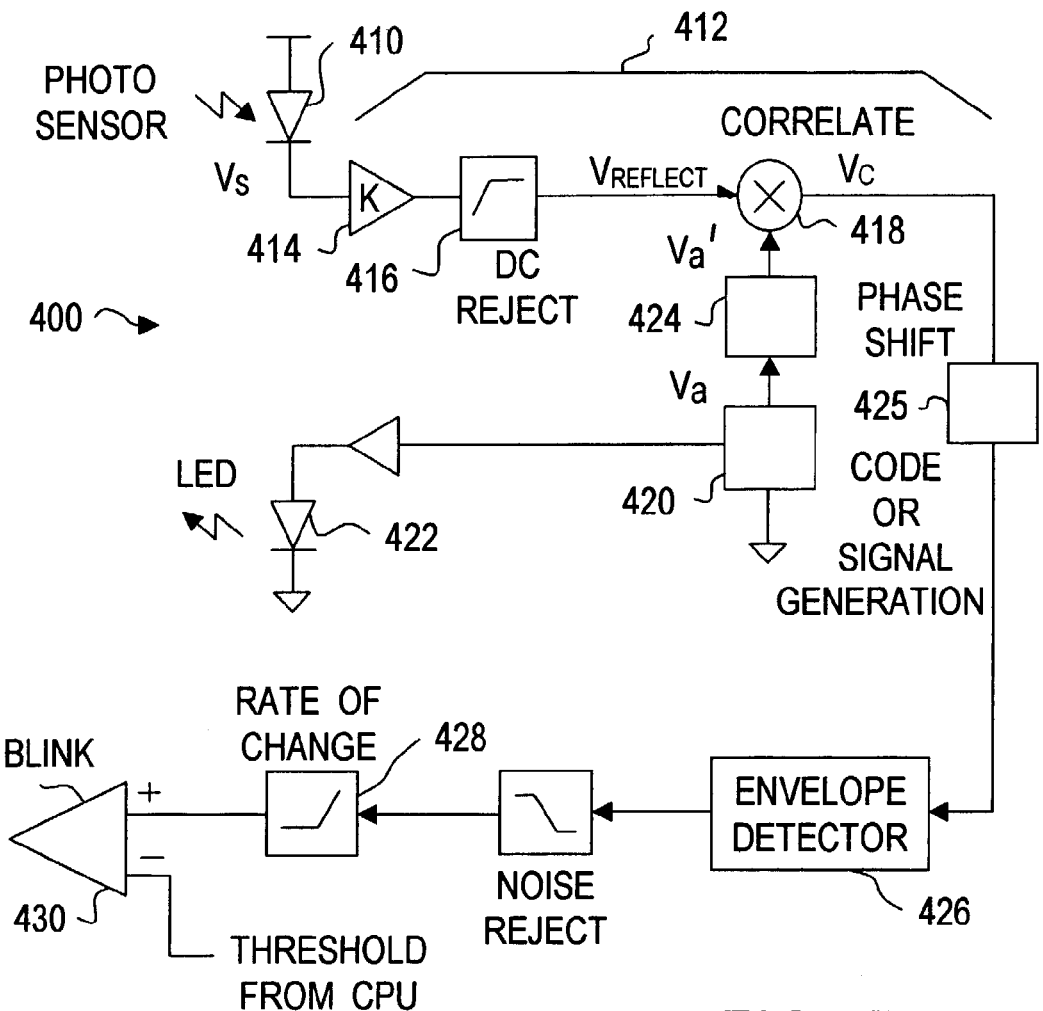
FIG. 5 is a signal pathway according to an embodiment of the method and device disclosed herein.

Referring now to FIG. 5, there is depicted an exemplary circuit 400 for ascertaining the eye-open and eye-closed states in an eye-blink event based on visual reflectivity. A photosensor 410 is associated with a suitable generalized amplifier 412. As depicted in FIG. 5, the generalized amplifier 412 can include a suitable mechanism for blocking ambient gain as at 414 together with a DC reject 416. The DC reject can be a suitable device or electronic program or code. In the circuit 400 as depicted, the signal produced by the photosensor 410, the DC reject 416 is a high pass filter. The generalized amplifier 412 as depicted also includes a suitable multiplier 418 which receives the signal produced by photosensor 410 as well as an attenuated signal from oscillator 420 as to the value of visual light generated by LED 422. The oscillator 420 can function to provide regular modulation or pseudo-random-modulation of the signal associated with the emitted light. The transmitted light signal $V_a$ received from oscillator can be processed through a suitable filter 424 to produce a phase-shifted signal. The multiplier 418 can provide a signal that correlates the transmitted and received signal to represent transmission of light from the LED 422 to the photosensor 410. The signal can be processed by a suitable antialiasing filter as at 425 with suitable signal magnification or amplification to provide a suitable digital signal that can be provided to an analog to digital converter (not shown). All processing can be done using digital signal processing utilizing a digital processor such as a microprocessor. The signal can be provided to a suitable digital signal processor such as control electronics 16.

In the circuit as depicted in FIG. 5, the signal is also processed through a suitable noise rejection device such as envelope detector 426 that is capable of ascertaining modulation in the reflected signal due to various phases of the eye-blink event. The signal can also be processed through a suitable differentiator(s) 428, which function as a rate of change differentiator. Suitable envelope detectors and rate of change differentiators can be configured to eliminate or minimize extraneous distribution which may result from reflection detected from peripheral elements such as eyelashes and the like and to ascertain actual rates of change associated with eyeblink events from changes due to distortion or the like.

The circuit also includes a suitable comparator 430 which permits comparison of $V_c$ as filtered through envelope detector 426 and differentiator 428 with suitable threshold values derived from a suitable source such as control electronics 16 or a suitable remote processing device.

The signal received ($V_s$) is considered to be a combination of reflected light ($V_{reflect}$) and ambient noise ($V_{noise}$) according the equation $$V_s = V_{reflect} + V_{noise} \tag{I}$$

Multiplier 418 is employed to provide a correlated signal ($V_c$) that is designed to exclude signals that interfere with the reflected signal ($V_{reflect}$). $V_c$ is the correlation of $V_{reflect}$ and the attenuated signal ($V_a'$) received from LED 422 through oscillator 420 according to the equation $$V_c = (V_{reflect} + V_{noise}) V_a' \tag{II}$$

The correlated signal can be processed to reject noise portions of the signal. Variation in the signal response can be analyzed for rate of change with upper and lower threshold values being provided from an external source such as control electronics 16 to translate the rate of change into signal commands relating to the eye-blink event being monitored.

Figure 6:
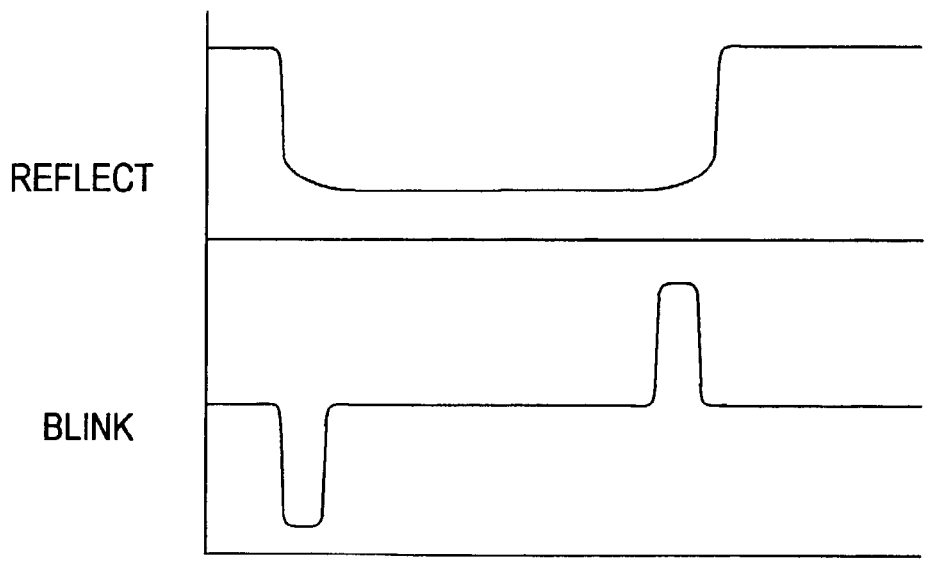
FIG. 6 is a graphic depiction of reflection versus eye-blink response.

Relationship between eye-blink event and rate of change in reflected light is schematically depicted in FIG. 6 in which a negative change in reflectance signals the initiation of the eye-open interval at eyelid retraction and a positive change in reflectance signals the termination of the eye-open interval with eyelid extension.

Information regarding eye-open and eye-closed intervals can be collected and processed to provide baseline data to generate an actuation command actionable on the electronically controllable fluid delivery element.

Figure 7:
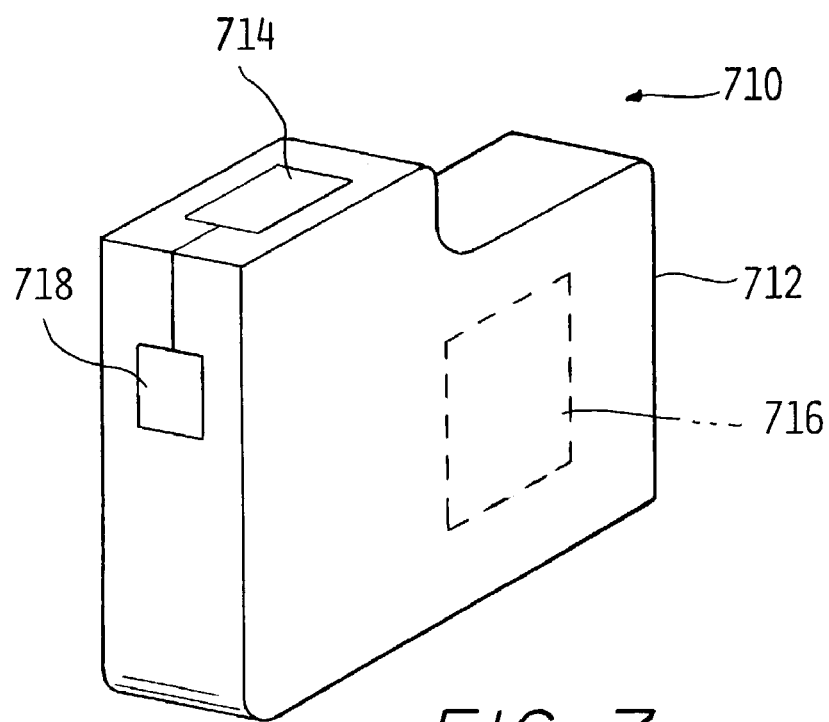
FIG. 7 is a perspective view of an embodiment of a cartridge for use in an ophthalmic dispensing device according to one of the alternate embodiments disclosed herein.

The dispensing device 10 may either disposable or configured to be reusable either by appropriate refilling mechanisms or by receiving suitable cartridges adapted to be removably fit into a suitable device equipped with a detector for ascertaining eye-open state. As depicted in FIG. 7, the cartridge 710 can include a housing 712 adapted to be removably received in an ophthalmic dispensing device. The cartridge 710 also includes an electronically controllable fluid delivery element 714 in communication with a reservoir 716 containing at least one ophthalmologically compatible material. The cartridge 710 can also include a suitable integrated circuit 718 which may contain data relevant to the content and/or operation of the cartridge 710. The integrated circuit 718 is configured to interactively communicate with elements such as control electronics to implement material delivery.

Figure 8:
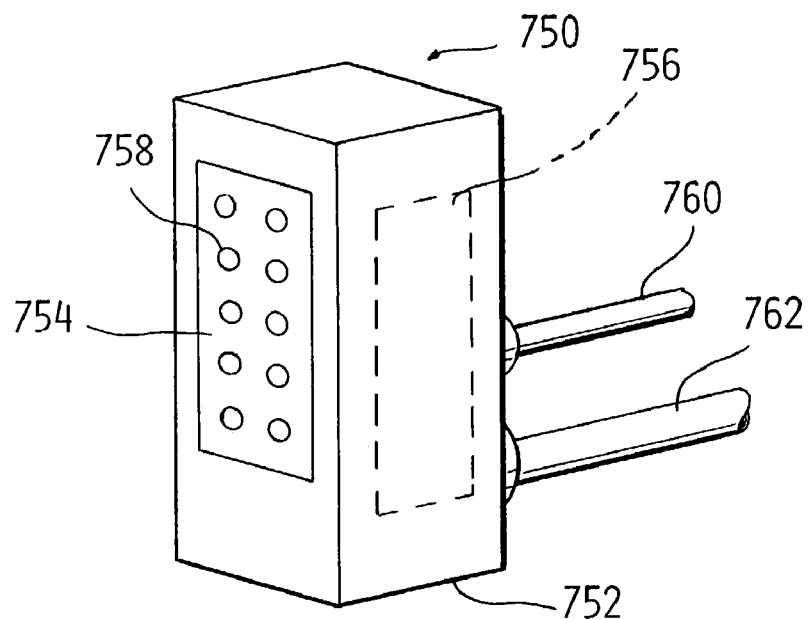
FIG. 8 is a perspective view of an alternate embodiment of a cartridge for use in an ophthalmic dispensing device as disclosed herein.

An alternate cartridge 750 is depicted in FIG. 8. The cartridge 750 includes a housing 752 adapted to be removably received in an ophthalmic dispensing device. The cartridge 750 includes an electronically controllable fluid delivery element 754 in communication with a collection reservoir 756. The electronically controllable fluid delivery element 754 may be configured with a suitable number of nozzle members 758 to permit ejection of fluid as desired or required. The nozzle members 758 be capable of independent actuation as desired or required or may be capable of actuation in any combination or sequence appropriate for material delivery. The cartridge 750 can also include at least one suitable fluid conveyance conduit 760 which can be permanently affixed or removably attachable to the cartridge 750 to permit conveyance of material to the collection reservoir 756 for delivery to the eye. Also included is a suitable electronic/electrical communication cable 762 establishing electrical and/or electronic communication between the cartridge 750 and sources remote to it.

It is contemplated that the device and method as disclosed herein can be employed to deliver various treatment materials including, but not limited to, dose-response critical material. As used herein, the term "dose-response critical material" is defined as material that elicits a detectable physical response evidenced in one or more optic structures. Such responses may be the purpose for which the material was employed or can be utilized to determine appropriate dose administration levels. For example, muscle relaxants and various dilation compounds can override the constriction reflex response present in the iris of the eye and permit dilation of the pupil opening for examination of interior optic structures. The effect of pupil dilation compounds is both dose-dependent and time-dependent. A threshold amount of material is necessary to achieve the desired response; however, the response may be time-delayed depending on factors such as tissue uptake rates, system response lags, and the like. Recovery can also be dose-dependent and time-dependent. The material administered to the eye will continue to elicit the dose-response until fully cleared from the optic tissue. Clearance time is dependent on concentration and/or amount of material administered.

The method as disclosed herein can be employed to administer material on a dose-response driven protocol. Thus, the amount of material which is administered to the optic structure can be varied based upon exhibited dose response, thereby minimizing the amount of material administered to that amount necessary to achieve the desired threshold dose response, such as pupil dilation.

Figure 9A:
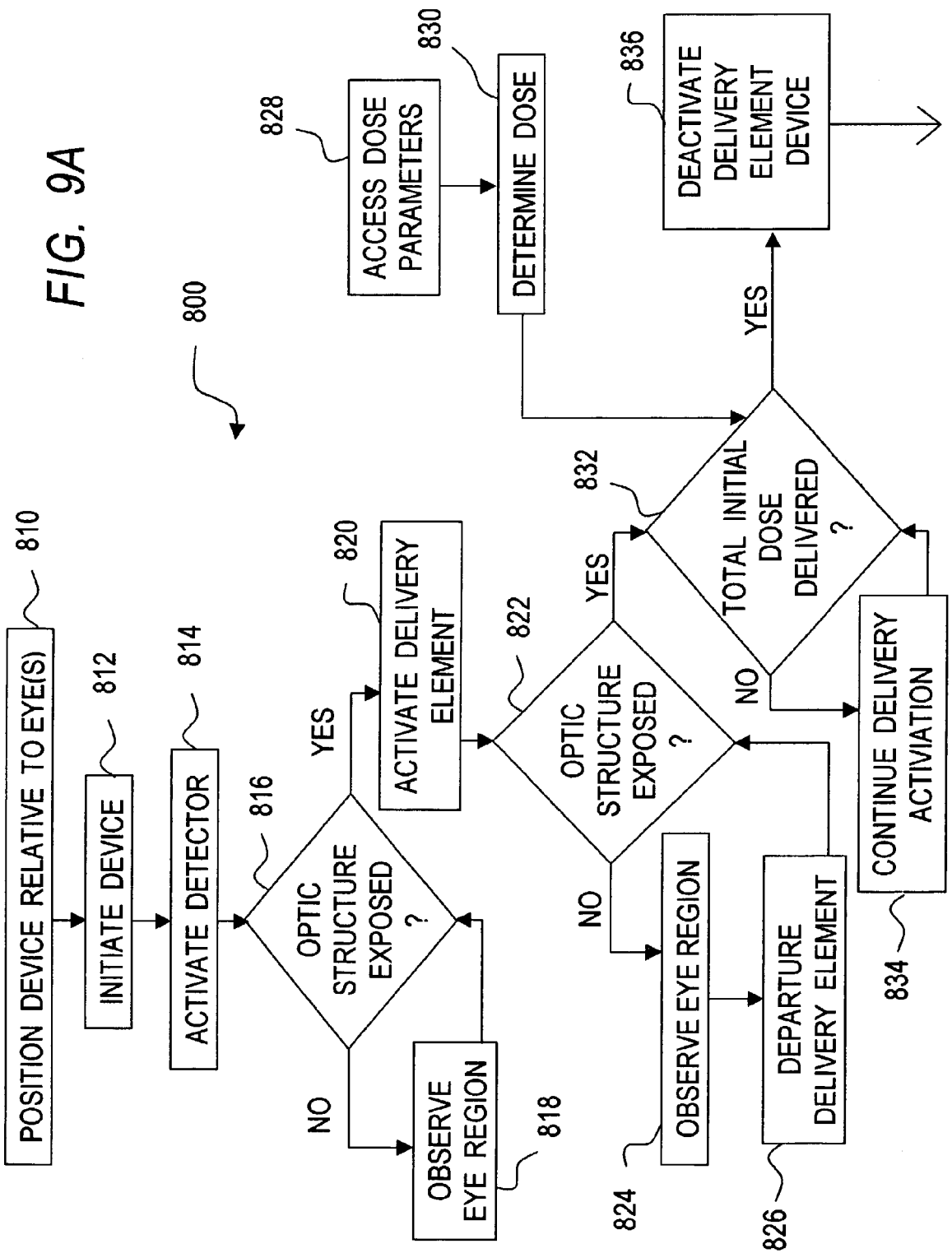
FIGS. 9A and B is a process diagram of a dose response administration method of an alternate embodiment of the method as disclosed herein.
Figure 9B:
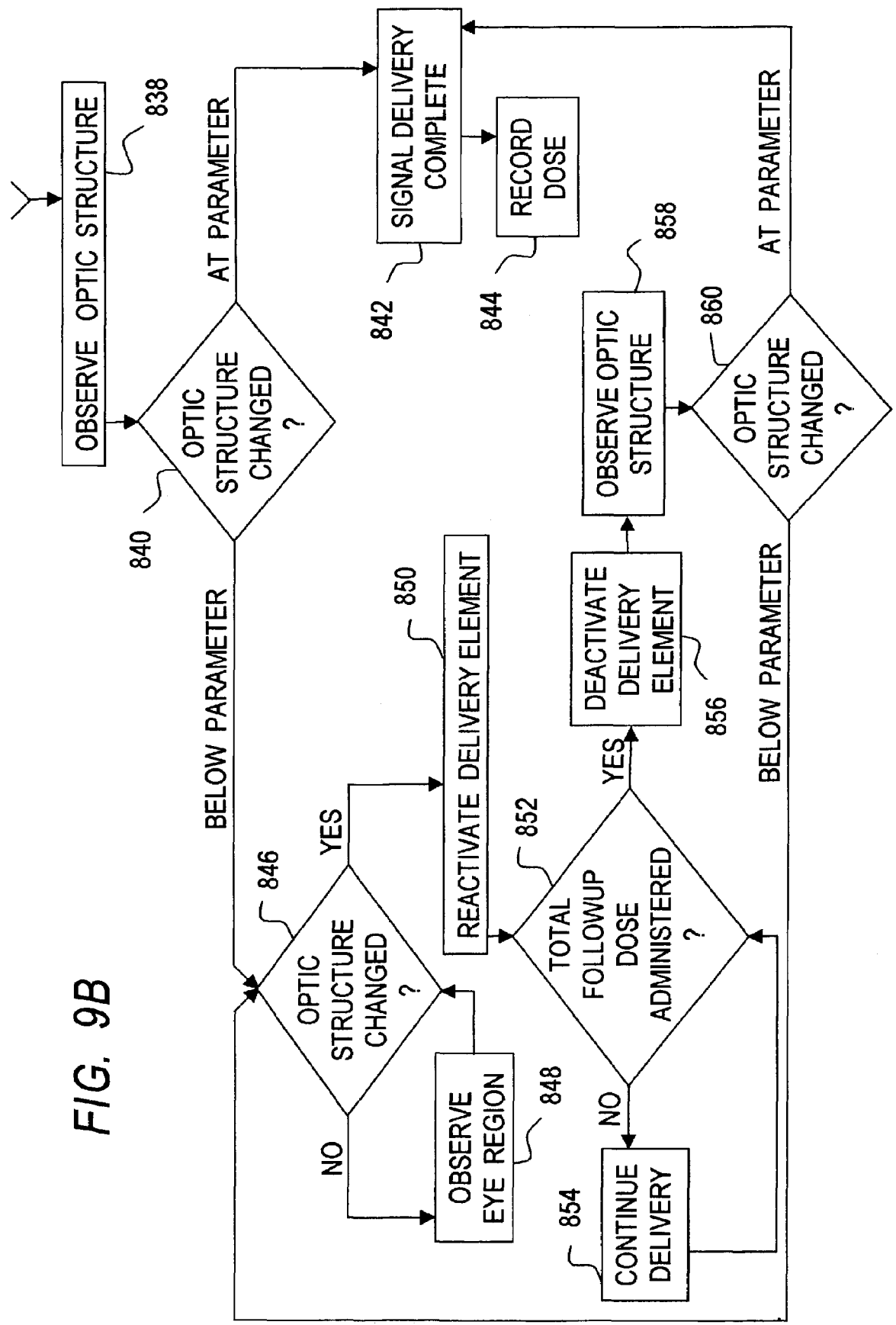

Referring now to FIGS. 9A and B, there is disclosed a process for administering material in a dose response control pattern. The process 800 commences with the positioning of the device relative to the eye or eyes as at reference numeral 810. The device is initiated as at reference numeral 812 after positioning has been ascertained. Once the device is initiated, the detector is activated as at reference numeral 814 to ascertain whether the targeted optic structure is exposed as at decision junction 816. If the optic structure is not exposed, the eye region is observed as at reference numeral 818 until the optic structure is positively exposed.

Upon exposure of the optic structure, the delivery element is activated as at reference numeral 820. Activation of the delivery element continues while the optic structure is exposed until the total initial dose is delivered. The initial dose amount or quantity can be determined by such factors as patient age, optic condition, etc. and is typically a portion of an amount determined to be total average dose.

The detector device continues to ascertain whether the optic structure is exposed during administration of the initial dose as at decision junction 822. If the optic structure is not exposed, the eye region is observed as at reference numeral 824 and the delivery element is deactivated as at reference numeral 826. Total initial dose amounts can be determined by accessing dose parameters contained in suitable data storage either associated with the device or external to the delivery device as at reference numeral 828. The amount of material delivered is compared against the determined dose as at reference numeral 830 to ascertain whether total dose is delivered as at decision junction 832.

If the total initial dose is not delivered, the activation of the delivery device is continued as at reference numeral 834. If the total initial dose has been delivered, the delivery element is deactivated as at reference numeral 836 and the optic structure is observed to determine whether a change is detected in the optic structure as at reference numeral 838. The parameters for determining whether the optic structure has changed as at decision junction 840 can be accessed from appropriate storage libraries contained in the device or external thereto. Additionally, the optic structure change can be one that is determined from initial observation of the structure performed during the initiation step 812. If optic structure change is noted, the change can be observed to ascertain whether the change is at parameter. If the change is at parameter, a signal that dosage delivery is complete can be produced as at reference numeral 842 and the dose recorded as at reference numeral 844.

If the change in optic structure is below parameter, further observation can proceed to ascertain whether the optic structure is exposed as at decision junction 846. If the optic structure is not exposed, observation of the eye region can occur as at reference numeral 848 until positive optic structure exposure has been ascertained. After optic structure has been exposed, the delivery element can be reactivated as at reference numeral 850 to deliver a follow-up dose. The amount of material employed in the follow-up dose can be determined from appropriate dose parameters contained in appropriate data storage in the ophthalmic delivery device or external thereto and will typically be a portion of the total average dose. The activation of delivery device continues until the follow-up dose has been delivered as at decision junction 852. Delivery can continue as at reference numeral 854 through multiple eye-blink events if necessary. Once the total follow-up dose has been delivered, the delivery element can be deactivated as at reference numeral 856 and the optic structure observed for change as at reference numeral 858. Assessment of the change in optic structure can occur at decision block 860. If the change in optic structure is at parameter, a signal that delivery is complete can be produced as at reference numeral 842 and the dose recorded. If the optic structural change is below parameter, the process can be repeated with multiple follow-up doses until the change in optic structure is detected. In this way, a dose-responsive drug can be calibrated to the individual responsiveness of the patient thereby avoiding over-dose and unpleasant side effects.

It is contemplated that observation and dose delivery can occur in concurrent or sequential steps depending upon the nature of the material delivered, the nature of the dose response observed, and the like.

While the invention has been described in connection with what is presently considered to be the most practical and preferred embodiment, it is to be understood that the invention is not limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as permitted under the law.

What is claimed is:

1. A device for administering material to an eye, the administering device comprising:
    an electronically controllable fluid delivery element; and
    a detector in electronic communication with the electronically controllable fluid delivery element, the detector configured to discern at least one portion of an eye-blink event and produce a signal actionable on the electronically controllable fluid delivery element;
    wherein the actionable signal initiates ejection of at least one material from the electronically controllable fluid delivery element during an eye-open portion of the eye-blink event.

2. The device of claim 1 wherein the material ejected is a fluid suitable for contact with the eye.

3. The device of claim 2 wherein the material has at least one of therapeutic capabilities and diagnostic capabilities.

4. The device of claim 1 wherein the at least one portion of the eye-blink event is at least a portion of the eye-open portion of the eye-blink event, and wherein the electronically controllable fluid delivery element is a microfluidic jetting device.

5. The device of claim 1, further comprising control electronics having an information storage portion, the control electronics in communication with the electronically controllable fluid delivery element and the detector.

6. The device of claim 5 wherein the control electronics includes a logic-processing unit.

7. The device of claim 6 wherein the logic processing unit includes at least one of a central processing unit and an application specific integrated circuit.

8. The device of claim 6, further comprising a chronometric device, the chronometric device in electronic communication with the control electronics.

9. The device of claim 1 wherein the detector includes a sensor capable of detecting at least one characteristic of an eye-blink event.

10. The device of claim 9 wherein the detector further comprises at least one emitter capable of generating at least one analytic waveform.

11. The device of claim 1, further comprising a spacer, the spacer configured to maintain a distance between the electronically controllable fluid delivery element and the eye.

12. A device for administering material to an eye, the administering device comprising:
    an electronically controllable fluid delivery element; and
    a detector in electronic communication with the electronically controllable fluid delivery element, the detector configured to discern at least one portion of an eyeblink event and produce a signal actionable on the electronically controllable fluid delivery element, wherein the detector is capable of ascertaining at least a portion of the eye-open portion of the eye-blink event, wherein the electronically controllable fluid delivery element is a microfluidic jetting device, and wherein the microfluidic jetting device is at least one of a thermal jetting device and a piezoelectric jetting device.

13. The device of claim 12 wherein the electronically controllable fluid delivery element is positioned to deliver fluid material to a location on an anterior region of the eye.

14. A device for administering material to an eye, the administering device comprising;
    an electronically controllable fluid delivery element; and
    a detector in electronic communication with the electronically controllable fluid delivery element, the detector configured to discern at least one portion of an eye-blink event and produce a signal actionable on the electronically controllable fluid delivery element;
    wherein the electronically controllable fluid delivery element functions during at least a portion of at least one eye-open portion of the eye-blink event.

15. A device for administering material to an eye, the administering device comprising:
    an electronically controllable fluid delivery element;
    a detector in electronic communication with the electronically controllable fluid delivery element, the detector configured to discern at least one portion of an eye-blink event and produce a signal actionable on the electronically controllable fluid delivery element;
    control electronics having an information storage portion, the control electronics in communication with the electronically controllable fluid delivery element and the detector; and
    a trigger switch, the trigger switch capable of being activated by a user, the trigger switch actionable on at least one of the control electronics, detector, and electronically controllable fluid delivery element.

16. A device for administering material to an eye, the administering device comprising:
    an electronically controllable fluid delivery element; and
    a detector in electronic communication with the electronically controllable fluid delivery element, the detector configured to discern at least one portion of en eye-blink event and produce a signal actionable on the electronically controllable fluid delivery element, wherein the detector includes:
        a sensor capable of detecting at least one characteristic of an eye-blink event; and
        at least one emitter capable of generating at least one analytic waveform, wherein the analytic waveform is at least one of an optical waveform and an acoustical waveform.

17. The device of claim 16 wherein the sensor is configured to ascertain analytical waveform reflected from the eye.

18. The device of claim 17 wherein the waveform is reflected from at least one of an anterior optic structure and an eyelid.

19. The device of claim 18 wherein an actionable command is derived from a characteristic difference between the waveform reflected from the anterior structure of the eye and the waveform reflected from the eyelid.

20. A device for administering material to an eye, the administering device comprising:

an electronically controllable fluid delivery element; and a detector in electronic communication with the electronically controllable fluid delivery element, the detector configured to discern at least one portion of an eye-blink event and produce a signal actionable on the electronically controllable fluid delivery element, wherein the detector includes an emitter and a sensor, the emitter directing an analytic waveform toward a targeted optic structure and the sensor detecting at least one change in reflected wave based on reflection based on the eye-blink event.

21. The device of claim 20 wherein the emitter produces at least one of an optical waveform and an acoustic waveform.

22. A device for administering material to an eye, the administering device comprising:

an electronically controllable fluid delivery element, the electronically controllable fluid delivery element in communication with a source of at (east one material to be delivered to the eye;

a detector in electronic communication with the electronically controllable fluid delivery element, the detector capable of ascertaining an eye-open state and producing at least one signal actionable on the electronically controllable fluid delivery element; and control electronics in communication with the electronically controllable fluid delivery element and the detector, the control electronics configured to mediate the signal emitted by the detector and actionable on the electronically controllable fluid delivery element.

23. The device of claim 22 wherein the control electronics include an information storage portion, the information storage portion containing information pertaining to at least one of the eye-open state, material dosage administration and optic condition.

24. The device of claim 23 wherein the control electronics are capable of receiving data derived from the detector arid generating at least one command actionable on the electronically controllable fluid delivery element.

25. The device of claim 23 wherein the control electronics and information storage portion are configured to ascertain multiple eye-blink events and develop an activation command operable on the electronically controllable fluid delivery element based on at least one of eye-open state, optic surface fluid content, and optic tissue response.

26. The device of claim 22 wherein the detector is capable of discerning at least one characteristic correlative with the eye-open state.

27. The device of claim 26 wherein the correlative characteristic is at least one of change in light reflectance, change in thermal radiation, and change in sound reflectance.

28. The device of claim 26 wherein the detector includes an emitter capable of producing an analytic wave form, the analytic waveform including at least one of an optic waveform and an acoustical waveform.

29. The device of claim 28 wherein the emitter directs the analytic waveform to a region on an anterior potion of the eye.

30. The device of claim 22 wherein the material to be administered is a therapeutic liquid.

31. The device of claim 22 further comprising at least one alignment mechanism confirming alignment of the electronically controllable fluid delivery element and detector relative to the eye.

32. A device for administering material to an eye, the administering device comprising:

means for ejecting a quantity of material into contact with the eye; and means for ascertaining at least one eye-open state of the eye, the ascertaining means capable of interacting with the ejecting means to deliver material to the eye during the eye-open state.

33. The device of claim 32 wherein the material ejecting means is an electronically controllable fluid delivery element.

34. The device of claim 32 further comprising interactive with the material ejecting means and the means for ascertaining at least one eye-open state.

35. The device of claim 32 wherein the means for ascertaining at least one eye-open state includes means for directing at least one analytical waveform to a targeted location on the eye, the analytical waveform being at least one of an acoustic waveform and an optical waveform.

36. The device of claim 35 wherein the ascertaining means is capable of determining an eye-open state over multiple eye-open intervals.

37. The device of claim 36 wherein the eye-open state is determined as a function of difference in reflected analytical waveform between the eye-open state and an eye-closed state.

38. A method for administering material to en eye, the method comprising the steps of:

positioning a device in proximate alignment to the eye, the device including an electronically controllable fluid delivery element, a detector capable of ascertaining an eye-open state of the eye, the detector device generating at least one command actionable on the electronic fluid delivery element; and dispensing material from the electronically controllable fluid delivery element into contact with the eye during the eye-open state.

39. The method of claim 38 further comprising the step of recording a plurality of eye-blink events to ascertain eye-open state, the recording step occurring prior to the material dispensing step.

40. The method of claim 38 wherein the dispensed material is a therapeutic liquid.

41. The method of claim 38 wherein the electronically controllable fluid delivery element is at least one of a piezoelectric letting device and a thermal jetting device.

42. The device of claim 41 wherein the material transfer means is an electronically controllable jetting device.

43. The device of claim 41 wherein the material transferred is a therapeutic liquid.

44. The method of claim 39 wherein the recording step comprises the steps of:

emitting an analytical waveform directed toward the eye region; and analyzing a waveform reflected from the eye region, the reflected waveform occurring during, an eye-blink cycle including at least one eye-open interval and at least one interval where an eyelid covers the eye.

45. The method of claim 44 wherein the dispensing step occurs during at least one eye-open interval.

46. The device of claim 44 wherein the analytic waveform is at least one of an optical waveform and an acoustic waveform.

47. The method of claim 44 further comprising the steps of:

analyzing a portion of the eye for response to material dispensed into contact with the eye; and based on the response analyzing step, implementing one of a) discontinuing the dispensing step, or b) dispensing additional material from the electronically controllable fluid delivery element into contact with the eye.

48. The method of claim 47 whereby the analyzing step includes analyzing at least one characteristic observable during the eye-open interval of the eye-blink cycle.

49. A device for administering material to an eye, the device comprising:

means for transferring material from a storage reservoir to the eye;

means for electronically controlling operation of the material transferring means; and means for detecting an eye-blink event, the detecting means in communication with the electronic control means to generate at least one command operable to actuate the material transfer means during at least one eye-open state.

* * * * *

UNITED STATES PATENT AND TRADEMARK OFFICE
CERTIFICATE OF CORRECTION

PATENT NO. : 7,201,732 B2  Page 1 of 1
APPLICATION NO. : 10/412057
DATED : April 10, 2007
INVENTOR(S) : Daryl E. Anderson et al.

It is certified that error appears in the above-identified patent and that said Letters Patent is hereby corrected as shown below:

In column 20, line 1, in Claim 12, delete "eyeblink" and insert -- eye-blink --, therefor.

In column 20, line 14, in Claim 14, delete "comprising;" and insert -- comprising: --, therefor.

In column 20, line 46, in Claim 16, delete "en" and insert -- an --, therefor.

In column 21, line 19, in Claim 22, delete "at (east" and insert -- at least --, therefor.

In column 21, line 37, in Claim 24, delete "arid" and insert -- and --, therefor.

In column 21, line 54, in Claim 28, delete "wave form" and insert -- waveform --, therefor.

In column 22, line 25, in Claim 38, delete "en" and insert -- an --, therefor.

In column 22, line 44, in Claim 41, delete "letting" and insert -- jetting --, therefor.

In column 22, line 54, in Claim 44, after "during" delete ",".

Signed and Sealed this

Second Day of December, 2008

JON W. DUDAS
*Director of the United States Patent and Trademark Office*